US008814923B2

(12) United States Patent
Nissilä et al.

(10) Patent No.: US 8,814,923 B2
(45) Date of Patent: Aug. 26, 2014

(54) LIGHT DISPENSING APPARATUS

(75) Inventors: Juuso Nissilä, Ii (FI); Antti Aunio, Oulu (FI)

(73) Assignee: Valkee Oy, Oulunsalo (FI)

(*) Notice: Subject to any disclaimer, the term of this patent is extended or adjusted under 35 U.S.C. 154(b) by 0 days.

(21) Appl. No.: 13/418,856

(22) Filed: Mar. 13, 2012

(65) Prior Publication Data

US 2012/0253434 A1 Oct. 4, 2012

(30) Foreign Application Priority Data

Mar. 31, 2011 (FI) ................................. 20115306

(51) Int. Cl.
*A61N 5/06* (2006.01)
*A61B 5/04* (2006.01)
*A61B 5/055* (2006.01)
*A61B 5/0476* (2006.01)

(52) U.S. Cl.
CPC ........... *A61N 5/0618* (2013.01); *A61B 5/04012* (2013.01); *A61N 5/0622* (2013.01); *A61N 2005/0647* (2013.01); *A61B 5/04001* (2013.01); *A61B 5/055* (2013.01); *A61B 5/04008* (2013.01); *A61B 5/0476* (2013.01); *A61B 5/0555* (2013.01); *A61N 2005/0652* (2013.01); *A61N 2005/0659* (2013.01); *A61N 2005/0662* (2013.01); *A61N 2005/063* (2013.01)
USPC .................. 607/88; 607/91; 600/407; 606/12

(58) Field of Classification Search
None
See application file for complete search history.

(56) References Cited

U.S. PATENT DOCUMENTS

| | | | |
|---|---|---|---|
| 2002/0115929 A1* | 8/2002 | Machida ....................... | 600/410 |
| 2006/0135868 A1 | 6/2006 | Salomon et al. | |
| 2007/0060984 A1 | 3/2007 | Webb et al. | |
| 2007/0156453 A1* | 7/2007 | Frielinghaus et al. ............ | 705/2 |
| 2007/0179571 A1 | 8/2007 | De Taboada et al. | |
| 2009/0254154 A1 | 10/2009 | De Taboada et al. | |
| 2010/0121158 A1 | 5/2010 | Quevedo | |
| 2010/0161017 A1 | 6/2010 | Choi et al. | |
| 2011/0092781 A1* | 4/2011 | Gertner ........................ | 600/301 |

FOREIGN PATENT DOCUMENTS

GB 2256276 A 12/1992

OTHER PUBLICATIONS

J. Rodriguez Cossio, European Search Report from corresponding European Patent Application No. EP12162022, p. 1-2, Jun. 15, 2012.
Zhang, X., "An Integrated Measurement System for Simultaneous Functional Magnetic Resonance Imaging and Diffuse Optical Tomography in Human Brain Mapping", Rev Sci Instrum., vol. 77, No. 11. p. 1-18 (Nov. 2006).
Jesper Lundbom, Finnish Search Report for corresponding Finnish Application No. 20115306, p. 1-2, Nov. 25, 2011.
Finnish Office Action issued for Application No. 20115306 dated Sep. 18, 2013.

* cited by examiner

*Primary Examiner* — Lynsey Crandall
(74) *Attorney, Agent, or Firm* — Hoffmann & Baron, LLP

(57) ABSTRACT

There is provided an apparatus, a method and a computer program. The apparatus comprises medical imaging unit for generating a group of voxel values of a patient, a voxel value representing an electromagnetically detectable functional state in a brain voxel of the patient, data processing unit for generating from the group of voxel values of the patient an indication that represents a level of a specific medical disorder of the patient, and illumination unit for directing non-invasively a dose of light to the brain of the patient.

19 Claims, 3 Drawing Sheets

LIGHT DISPENSING APPARATUS

CROSS-REFERENCE TO RELATED APPLICATION

This application claims priority based on Finnish Application No. 20115306, filed Mar. 31, 2011, which is incorporated herein by reference in its entirety.

BACKGROUND

1. Field

The present invention relates to medical devices and more specifically to an apparatus configured to direct non-invasive dosing of light to the brain of a patient.

2. Description of the Related Art

A medical disorder refers here to an abnormal physiological or psychiatric condition affecting the body or mind of a human person. Recently a number of medical disorders have been found to be responsive to light that is directed to brain cells of the affected person. Light therapy is already widely accepted as a treatment for, for example, Seasonal Affective Disorder and has solid clinical evidence across a number depressions such as PMS, Postpartum Stress and Post-Traumatic Stress Disorder. Recently, light therapy has also provided promising evidence in a number of Central Nervous System (CNS) conditions such as Alzheimer's Disease, Parkinson's disease and even migraine.

The problem with implementations of light devices for treatment of physiological disorders is that there is yet little knowledge on areas of the brain that are affected in abnormal conditions and/or responsive to illumination. In addition, delivery of light to the internal structures of the brain is very difficult to manage and control. Light therapy in its current form is therefore typically administered inaccurately and in excessive amounts.

In addition, it is considered possible that there may be further medical disorders that are responsive to non-invasive light therapy and could be treated with illumination applied through the skull of the patient. However, it is difficult and very time-consuming to identify them and verify the efficacy of light treatment through testing groups of diagnosed patients.

SUMMARY

An object of the present invention is thus to provide a solution to overcome or at least alleviate the above problems. The object of the invention is achieved by an apparatus and a method implemented by the apparatus, which are characterized by what is stated in the independent claims. The preferred embodiments of the invention are disclosed in the dependent claims.

The invention is based on integrating in an apparatus measurement means for determining from the brain of a patient a level of a specific medical disorder, and illumination means for directing non-invasively a dose of light to the brain of the patient such that both these means can be applied on a patient during one therapeutic session. Due to the proposed configuration, the response to administered light therapy may be measured directly after the treatment. Detected effect of the treatment may then be used to control the delivery and/or dose of light directed to the patient. In addition, one may use the invented configuration to test effects from illumination to various medical disorders to find further conditions that could be treatable with light therapy.

BRIEF DESCRIPTION OF THE DRAWINGS

In the following, embodiments will be described in greater detail with reference to accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

A number of medical disorders of a patient are related to functional states of internal structures in the brain, for example, abnormal internal structures or functional behavior the brain. Electromagnetic techniques enable analysis of internal structures of the brain. For example, a magnetic resonance imaging (MRI) device applies a strong magnetic field to align magnetization of some atoms in a brain region, and systematically alters the alignment of this magnetization with radio frequency fields. The nuclei of the atoms generate a rotating magnetic field that can be detected with a scanner. This detected information may then be recorded and used to construct an image of the scanned brain region.

Functional states of scanned internal structures can also be detected and analyzed for functional inference of some neurological and psychiatric diseases. Functional state in this context refers to state of an operational internal entity and corresponds with a mode of operation of such a structure. As an example, functional MRI (fMRI) enables detection of task reponses as well as spontaneous interregional connectivity assessment of a human brain without invasive or radioactive methodology.

Figure 1:
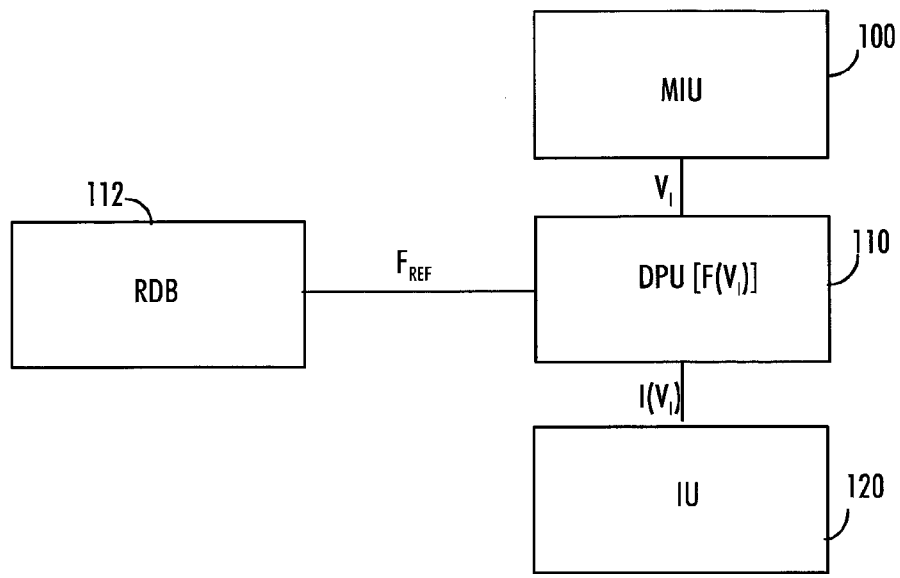
FIG. 1 illustrates units of an embodiment of an apparatus.

The block chart of FIG. 1 illustrates units of an embodiment of an apparatus according to the present invention. The apparatus comprises measuring means for generating a group of voxel values of a patient. In FIG. 1, these measuring means are shown as a medical imaging unit 100, a device that manipulates with defined electromagnetic fields a region within a patient's body, and produces a detectable, spatially encoded signal that represents the functional state of brain cells within the region. The spatial encoding is three-dimensional and implemented by dividing the region into a regular grid of volume elements, voxels.

The medical imaging unit 100 in the exemplary embodiment of FIG. 1 is an fMRI unit, without limiting the invention to this particular imaging type. Other measuring methods that allow provision of spatially encoded signals that represent structural or functional state of brain cells may be applied, correspondingly. Examples of such methods include Positron Emission Tomography (PET), Positron Emission Tomography—Computed Tomography (PET-CT), ultra sound scanning, magnetoencephalometry (MEG) and electro-encephalography (EEG).

Medical imaging devices applying MRI and fMRI are widely in use and thoroughly documented, and their implementation, as such, is well known to a person skilled in the art. As a brief introduction, MRI produces signals from a region by means of three electromagnetic fields: a strong static magnetic field that directs hydrogen nuclei within the region, weaker time-varying gradient fields for spatial encoding, and a weak radio-frequency (RF) field that manipulates the hydrogen nuclei such that signals are produced. In the strong magnetic field, protons of the hydrogen nuclei align with the direction of the magnetic field. When the RF field is added, protons absorb energy and start to change orientation of their spin. After the RF field is turned off, the protons decay to their original spin state and the difference in energy between the two states is released as a photon. The electromagnetic signal of these photons can be detected as radio waves. Time-varying gradient fields are applied to the region during the scan to make the magnetic field strength depend on the position within the region. This makes the frequency of the released photons dependent on their original position in a predictable manner, and position information can be recovered from a signal by means of a Fourier transform. Protons in different tissues return to their equilibrium state at different rates, and this difference can be detected with coils that are sensitive to variations of transverse magnetization vector.

The fMRI medical imaging unit 100 of FIG. 1 operates on a measurement region incorporating at least part or the whole of a brain of a patient. The measurement region is arranged into a three-dimensional grid of volume elements. During measurement, the measurement region is scanned with a specific combination of radiofrequency pulses and gradients that form a defined sequence. Data is collected with sequence parameters that are sensitive to changes in magnetic susceptibility. These changes correspond with changes in blood-oxygen-level (BOLD) contrasts in the region, and signals carrying data on them are referred to as BOLD signals. Increased neural activity causes an increased demand for oxygen, and the vascular system increases the amount of oxygenated hemoglobin relative to deoxygenated hemoglobin. Magnetic susceptibility of blood quite closely matches the tissue magnetic susceptibility, so increased BOLD signal intensities arise from increases in the concentration of oxygenated hemoglobin. Accordingly, a vascular response in a voxel leads to a change in magnetic susceptibility in that voxel and this change manifests itself as a detectable change in the BOLD signal. In the present embodiment, a value of a BOLD signal for a voxel thus corresponds to a voxel value that represents an electromagnetically detectable functional state in a brain voxel of the patient.

The apparatus of FIG. 1 comprises also detecting means for generating from the group of voxel values collected from the patient an indication that represents a level of a specific medical disorder of the patient. In the embodiment of FIG. 1 the detecting means are represented by a data processing unit 110 that is connected to the medical imaging unit 100. Voxel values $v_i$ generated in the medical imaging unit 100 are input to the data processing unit 110, undergo a procedure $F(v_i)$ that matches the voxel values with reference data $f_{REF}$ of at least one medical disorder, and transforms the voxel values into an Indication $I(v_i)$ that corresponds with the level of that medical disorder.

The reference data $f_{REF}$ may be based on measurement results collected from a group of test subjects, or on an algorithm decoding the voxel values in a predefined way. The present embodiment applies history data collected from a sequence of specific measurements performed to a selected group of test subjects. A majority of early functional brain mapping with fMRI has been directed toward assessing locations of brain activations during a psychological task. However, fMRI also facilitates analysis of connectivity that infers from data acquired during a resting state. It has been noted that during a resting state, there is spontaneous activity of neurons, and such spontaneous activity is followed by regional cerebral blood flow increases. Neural activity in a specific brain area affect remotely located neurons in other brain areas through an efferent output. Temporal similarities in BOLD signal fluctuations detected in a resting state can thus be interpreted to reflect functional connectivity of different brain regions.

Resting-state functional connectivity analyses study similarities in temporal behavior of blood oxygen level dependent (BOLD) signal fluctuations in different brain regions. Coherent spatial patterns of low-frequency (<0.1 Hz) fluctuations in a resting-state BOLD signal are referred to as a functional network. Alterations in functional connectivity of such functional networks have been seen to precede some structural changes and clinical symptoms. The procedure $F(v_i)$ performed on input voxel values $v_i$ in the data processing unit 110 of FIG. 1 is thus based on analyzing temporal variations of functional connectivity in defined resting state networks (RSN) that are considered relevant in respect with a defined physical disorder. In the present embodiment the analysis is implemented by comparing behavior of measured functional connectivity in a defined group of RSNs of a patient to modeled behavior of functional connectivity in the same group of RSNs. The model is designed for detection of a specific medical disorder such that differences between the measured and modeled behavior may be considered to represent the current level of that specific medical disorder of the patient.

Figure 2:
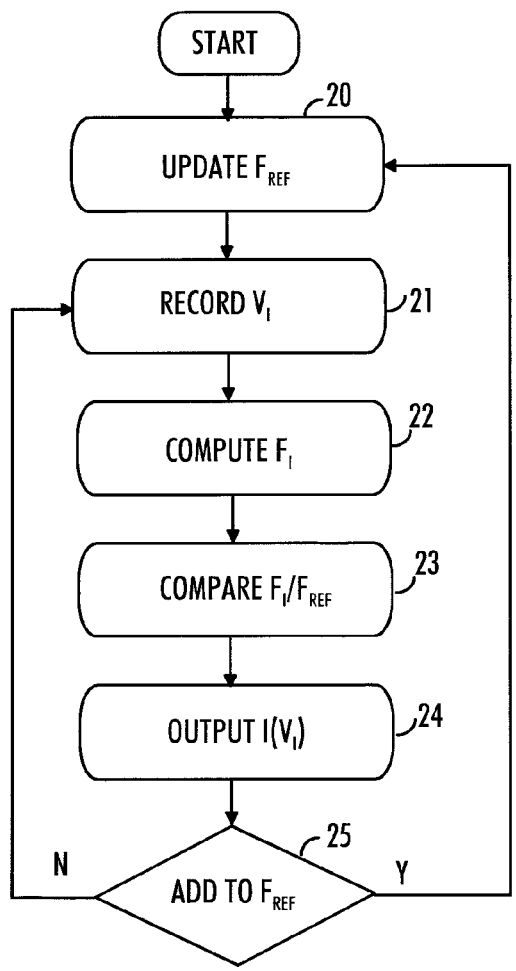
FIG. 2 illustrates stages of a procedure for generating an indication that corresponds with match between a measured voxel values and a predefined functional connectivity model.

FIG. 2 illustrates stages of a procedure $F(v_i)$ for generating an indication $I(v_i)$ that corresponds with match between a measured voxel values and a predefined functional connectivity model, and thus with a level of a specific medical disorder of the patient. The procedure is performed in the data processing unit 110 of FIG. 1. For modeling behavior of functional connectivity, the data processing unit 110 comprises a reference database 112. The procedure begins in a stage where the data processing unit 110 is switched on and in operative state. The reference database is updated (stage 20) with reference information $f_{ref}$ that provides a recorded functional connectivity model for a specific set of functional networks in a measured region. In this embodiment, the model is implemented by means of one or more datasets of functional connectivity values that are related to a defined medical disorder. In most cases, a plurality of datasets is applied in the model.

The relation between the defined medical disorder and data-sets of functional connectivity values may be established, for example, through a series of tests where voxel values are extracted from a selected group of test subjects. The selected group comprises a group of patients diagnosed with the defined medical disorder and a group of healthy control subjects. Functional connectivity values of the group of patients are compared to functional connectivity values of the group of healthy control subjects. If similar alterations in some functional networks are detected in the group of test subjects, these alterations may be considered to be related to the defined medical disorder.

For example, seasonal affective disorder (SAD) is considered as a sub-type of recurrent major depressive disorder (MDD) or bipolar affective disorder in which depressive episodes regularly begin in one season and remit in another season. The winter-type of SAD manifests as atypical symptoms of depression that recur in the fall and winter, such as depressed mood, anhedonia, decreased activity, decreased libido, hyperphagia, hyper somnia, carbohydrate carving, fatigue and weight gain. It is considered possible that functional connectivity alterations related to SAD exist in brain regions earlier reported to involve metabolic changes in SAD patients. For provision of reference information applicable in detection of SAD, fMRI has been used to collect test data from 45 medication-free subjects with SAD, and 45 age-, gender—(39.78±10.64, 30 ♀, 15 ♂) and ethnicity-matched healthy control subjects (no concomitant medications) from the general population. The test groups were imaged with fMRI using a same test protocol during one winter-period. All subjects with SAD were scanned within one week after they were diagnosed.

During measurements, resting-state BOLD data were collected on a whole body fMRI system with an eight channel receive coil, using a defined sequence (EPI GRE sequence: TR 1800 ms, TE 40 ms, 280 time points, 28 oblique axial slices, slice thickness 4 mm, inter-slice space 0.4, whole brain coverage, FOV 25.6 cm×25.6 cm, with 64×64 matrix, parallel imaging factor 2, flip angle 90°). T1-weighted scans were imaged using 3D FSPGR BRAVO sequence (TR 12.1 ms, TE 5.2 ms, slice thickness 1.0 mm, FOV 24.0 cm, matrix 256× 256, and flip angle 20°, and NEX 1) in order to obtain anatomical images for co-registration of the fMRI data to standard space coordinates. For resting state, the subjects were instructed to simply lay still inside the scanner with their eyes closed, think of nothing particular and not to fall asleep. Motion was minimized using soft pads.

Independent Component Analysis (ICA) is a well-known blind source separation technique that may be used as a data-driven analysis tool for processing fMRI-generated voxel values. It has been shown that by increasing the number of ICA estimated sources, one can probe the entire brain cortex with finely detailed sub-networks. ICA allows differentiating relevant functional brain signals from various sources of noise without a priori knowledge of the signal origin. It also separates noise sources from detected data and then provides spatial maps of functionally independent brain networks.

In the exemplary tests the results revealed that SAD patients compared to age-, gender- and ethnicity-matched healthy control subjects showed statistically significant increases in functional connectivity involving several RSNs. SAD-related increased functional connectivity was shown at two different functional levels while mainly focusing on the detailed RSNs level (70 ICs). Large-scale functional brain networks were localized using low model order ICA of 20 components. Significant increases in functional connectivity were detected in 4 out of 11 identified RSNs in patients with SAD. Segmentation of the brain functionality into detailed sub-networks using a high model order ICA of 70 components yielded 47 RSNs. Significant increases in functional connectivity were detected in 25 RSNs out of the 47 identified networks. Datasets of spatial maps on the detected RNSs and/or of the RNSs of altered functional connectivity are thus applicable as reference information $f_{ref}$ related to a defined medical disorder, in this example the SAD.

The subsequent stages of the procedure of FIG. 2 form a diagnostic session applied on a patient. The diagnostic session refers here to a sequence of operations performed to the patient at one time such that each generated indication $I(v_i)$ unambiguously corresponds with a group of extracted voxel values $v_i$. In a diagnostic session, a defined brain region of the patient is scanned with the medical imaging device 100, voxel values $v_i$ of voxels in that brain region are recorded (stage 21) and input into the data processing unit 110.

The data processing unit computes (stage 22) from the group of voxel values one or more datasets $f_i$ that carry functional connectivity information for at least the functional networks applied for detection of the specific medical disorder in the reference information $f_{ref}$. It is known that so far use of ICA in analysis of fMRI signals applies measurements from a plurality (in the order of 20-40) of subjects. This is to provide a valid statistical power to assess RSNs of one medical disorder and to conclude their common features.

In order to enable evaluation a level of a specific functional disorder in the brain of the patient by applying ICA to voxel values collected with fMRI from a single patient, the computation in the exemplary embodiment of FIG. 2 may include a further multiplication process. The multiplication process includes a pseudoreplication stage where N pseudo datasets with voxel values having normally distributed variation compared to actually measured voxel values collected from the patient are generated. The rate N is selected according to the applied ICA model. The multiplication process may alternatively, or in addition to, include also a post-treatment stage where the N sets of pseudovoxel values are processed to show artificial stochastical variation in data such that a normally distributed variation in all or most parameters of measurement dataset is achieved. Therefore, the idea behind the multiplication and post-treatment stage is to add variation to the data on the voxel-level. This variation then causes the data of the patient to be "spread" by amount of a standard deviation to the positive direction and to the negative direction. The obtained pseudovoxel value sets form a dataset $f_i$ of the patient.

In an embodiment, the statistical variation to the data may be added in the following way: First, for each measured voxel value, a row of pseudovoxel values are generated. The pseudovoxel values are generated so that the more they differ from the measured pixel value, the less they are. In an example, as shown in Table 1, if the difference from the measured voxel value is −50, there are 2 pseudovoxel values generated, and so forth. It should be noted that the values presented in Table 1 are completely imaginary and the purpose is merely to illustrate the process according to the embodiment. By doing the generation of pseudovoxels this way, the resulting row may have a normal distribution, which is desired. The selection of the pseudovoxel values and the number of pseudovoxels to be generated depend on the deviation of the MRI-device, for example. Typically, the MRI-device has certain deviation per measurement point, which may be known or at least is possible to be acquired by means known to a skilled person.

TABLE 1

Exemplary relationships between the number of pseudo-voxels to be generated and the difference from the measured voxel value.

| Difference | −100 | −50 | −20 | −5 | −1 | 0 | 1 | 5 | 20 | 50 | 100 |
|---|---|---|---|---|---|---|---|---|---|---|---|
| #Pseudo-vox. | 1 | 2 | 5 | 15 | 25 | 35 | 25 | 15 | 5 | 2 | 1 |

The n pseudovoxel rows to be generated may equal to the number of measured voxels. Each row may have 2×(1+2+5+15+25)+35=131 samples. In other words, the original column vector of n measured voxel values is this way processed into 131×n-matrix, where each row of the matrix has normal distribution with a desired standard deviation.

Next, new data sequences are generated by randomly selecting one number from each row of the matrix. Thus, a unique data sequence with n values is obtained. Another unique data sequence is selected such that the values that have already been selected for another unique data sequence cannot be selected for the current sequence. In the example of Table 1, 131 unique data sequences are obtained. These unique data sequences form a dataset $f_i$ of the patient.

In another embodiment, the statistical variation is obtained by measuring the patient multiple times.

The one or more datasets $f_i$ of the patient from the diagnostic session are compared (stage 23) to the datasets $f_{ref}$ stored as reference information. Since the datasets of the reference information relate to the defined medical disorder, like SAD, the comparison produces a value that corresponds with level of similarity between datasets of functional connectivity $f_i$ collected from the patient and the reference datasets of $f_{ref}$. The comparisons may be implemented automatically and apply well known statistical and/or artificial intelligence methods, for example self-organizing maps (SOM). This level of similarity represents the level of the medical disorder of the patient, and may be out put as an indication $I(v_i)$ (stage 24) from the data processing unit 110. The indication $I(v_i)$ may be output, for example, in form of one or more values, one or more matrices or tables, or one or more images, or a combination of them. The indication may be output to the operator of the apparatus or to a subsequent functional unit of the apparatus.

It is noted that the present embodiment is provided merely to describe one method of generating from the group of voxel values of the patient an indication that represents a level of a specific medical disorder of the patient. The invention is not restricted to use of fMRI or ICA, or computational methods applied in implementations based on fMRI and ICA.

In an aspect of the embodiment, voxel values and results from the comparison of stage 24 may be fed back to the reference database. By means of this, reference information may be accumulated in the course of successive diagnostic sessions and the model converges towards greater statistical accuracy. Accordingly, the procedure may comprise a stage where the data processing unit decides (stage 25) whether to update the result of the generated indication $I(v_i)$ to the reference information or not. The decision may be automatic and based on a pre-defined rule, or may be implemented through a query from the operator of the apparatus. If the decision is positive, the procedure returns to stage 20, otherwise the procedure returns to stage 21 to be standby for a fresh set of voxel values.

The apparatus of FIG. 1 comprises also an illumination unit 120 that provides means for directing a dose of light to the brain of the patient. Light refers here to electromagnetic radiation that ranges in the visible spectrum from about 380 nm to about 780 nm, or in adjacent radiation regions of infrared and ultraviolet, which are not visible to the human eye. The illumination is administered non-invasively, i.e. via an ear canal, via non-ocular route around the eye or though the skull in any part of head. Illumination can be directed by means of a plurality of light units, such as LEDs. Illumination means may comprise also larger illumination devices, for example a traditional light box inserted on the head and against a targeted region of the brain.

Light therapy is widely accepted as a treatment for Seasonal Affective Disorder and has already solid clinical evidence across a number of other medical disorders. Examples of such are Premenstrual Syndrome, Postpartum Stress and Post-Traumatic Stress Disorder. Recently, light therapy has also provided promising evidence in a number of Central Nervous System conditions such as Alzheimer's Disease, Parkinson's Disease and even migraine. In light therapy light is directed to brain areas (a) where an abnormal neurobiological condition of the brain exists or (b) where light can trigger a cascade that cures the medical disorder detected elsewhere in the body targeted condition elsewhere Such cascade may comprise, for example, release of anti-inflammatory cytokines to be active in the other parts of the body or in the intracranial neural tissue itself.

A medical disorder that manifests through structural or functional changes in brain of a patient and is responsive to light therapy administered through the skull of the patient is effectively treated by means of the pre sent apparatus that provides integrated means for detecting changes in the brain and treatment by light therapy during one treatment session. A treatment session refers here to a sequence of operations performed with one apparatus, in which a patient lays on a base structure and remains positioned throughout the operations. Integration facilitates also verification of responsiveness of a medical disorder to a specific treatment (dose, route of delivery, etc.) with light.

Level of integration of the measuring means 100 and the illumination means 120 of the apparatus may vary, but essentially the integration is implemented such that both means may be applied on the patient during a treatment session. A practical problem of such integration is that most measuring means providing spatially encoded data from the brain are based on use of electromagnetic fields that do not allow existence of magnetic materials in the vicinity of the scanned regions. On the other hand, best results of light therapy are achieved with high intensity sources that are preferably administered via non-ocular routes. In such configurations, the light sources need to be positioned in the immediate vicinity of the skull of the patient. Therefore the measuring means and the illumination means are preferably integrated into the apparatus in such a manner that light may be delivered all the way to the skull of the patient without notable interaction with the electromagnetic fields applied by the measuring means.

Figure 3:
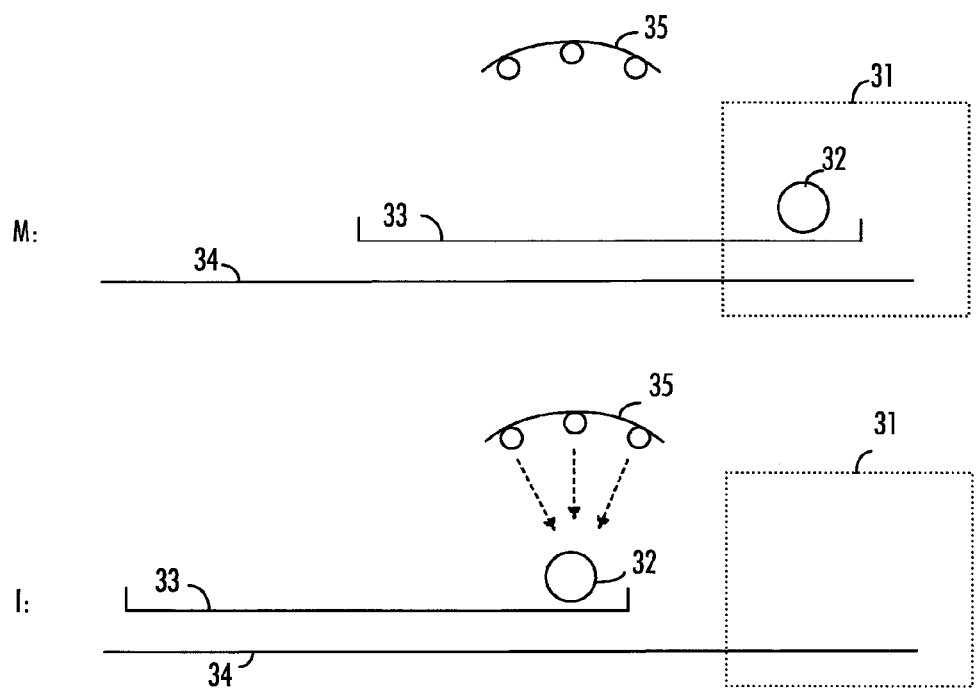
FIG. 3 shows an embodiment of integration between measuring means and illuminating means.

FIG. 3 shows an embodiment where interaction of the measuring and illuminating means is eliminated by a protective distance between them. FIG. 3 shows a measurement region 31 in which the skull of the patient 32 needs to be positioned for the measurement. In order to accomplish this, the apparatus comprises a cradle 33 on which the patient lies throughout a treatment session. The cradle 33 slides on a track 34 between at least two positions: a measuring position M and an illumination position I. During the diagnostic session of FIG. 2 the cradle 33 is kept in the measuring position M where the cradle extends outwards from the measurement region 31 such that the skull of the patient is within the measurement region. For the duration of the light therapy, the patient is moved in the cradle 33 away from the measurement position to the illumination position I where intensive light sources 35 may exist without interfering with strong electric or magnetic fields of the measurement region 31. The light sources may thus be directed to the immediate vicinity of the skull of the patient, and the effect of the light treatment may be measured within one treatment session. In this configuration, magnetic properties of materials of the light sources do not interfere with the fields and a wide variety of efficient light sources may thus be applied for the illumination.

Figure 4:
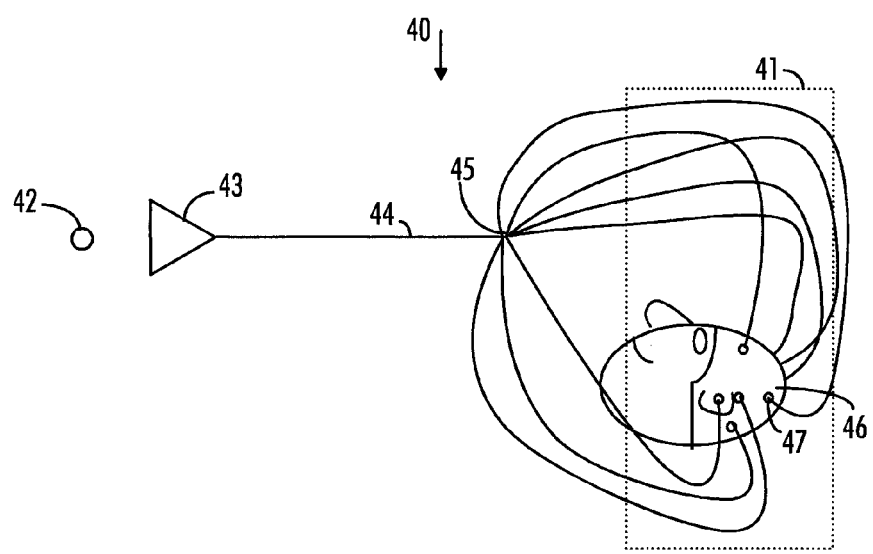
FIG. 4 shows another embodiment of integration between the measuring means and the illuminating means.

FIG. 4 illustrates another embodiment where integration of the means is facilitated by directing a beam of light on a patient along a transmission path that does not interact with the applied electrical or magnetic fields. This way the light treatment can be provided to the patent even if his brain coincides with the measurement region 41 where those fields are applied during the measurement. Accordingly, the apparatus of FIG. 4 comprises at least one light source 42 and a light distributer 40. The light distributer 40 provides electromagnetically non-interfering means for inputting a sequence of light from a source outside the measurement region 41 and outputting the sequence of light inside the measurement region 41.

In FIG. 4, the light source comprises a lamp 42 positioned outside the measurement region 41. The light router 43 is a helmet configuration made of electromagnetically non-interfering materials. The potentially electromagnetically interfering light source 42 may thus be located in a safe distance from the measurement region 41 and electromagnetic fields therein, and the helmet configuration may deliver light from the source to defined positions on the skull of the patient even at the time of measurement. The helmet configuration comprises an optical collector 43, a light router 44, an optical divider 45 and a releasable headpiece 46. The optical collector 43 is an element that absorbs light from the light source and concentrates the absorbed light into a beam that progresses into a defined direction. The light router 44 is an element that receives a light beam in one position and delivers the light beam along a defined route to another position. Here the light router 44 receives the light beam from the optical collector 43 and delivers it along a known route to a position near the patient's head. The light router 44 is typically made of an optical fiber and the dimensions of the fiber define the known route, but other electromagnetically non-interfering materials with light transmitting capability may be applied, as well. The optical divider 45 is an element that receives a light beam in one point and divides it into two or more beams that progress from the point of division along individual routes. Here the optical divides receives the light beam from the light router 44 and divides it into two or more beams that progress to the vicinity of the skull of the patient.

The releasable headpiece 46 is an element that comprises a rack of mechanically connected points of connection 47. The rack is convex to incorporate at least part of the head of the patient and adjustable in at last part of its dimensions such the rack stays in the head of the patient when it is fastened and comes off from the head of the patient when it is released. A weblike structure or one or more tightening straps may be applied to enable appropriate adjustment of the rack. Advantageously the position of each point of connection is well known or easily derivable, when the headpiece is fastened to cover the head of the patient. As shown in FIG. 4, the headpiece 46 may be configured to provide points of connection 47 also within the ear canal of the patient.

The peripheral branches of the optical divider 45 are connected to the releasable headpiece 46 such that the beams of light emitted from the peripheral ends of the optical divider are directed to the skull of the patient in the known positions of the connection points.

Due to the configuration, the patient may remain in one position throughout the diagnostic session and the light treatment, and diagnostic measurements may even be taken simultaneously with the light treatment. Different means implementing the measurements and the illumination do not, however, interfere with each other. Effect of various aspects of the treatment may be carefully monitored and recorded and efficacy of light therapy analyzed and verified.

It is noted that the helmet configuration is only one exemplary mechanism for implementation of a non-interfering transmission path. For example, the light router may comprise a mirror, positioned outside the measurement region 41. The lamp may be directed to emit a beam of light on the mirror and the mirror is focused to reflect the beam of light on a defined position of the skull of the patient. Furthermore, the helmet configuration may be applied for light therapy even in configurations that do not incorporate measuring and/or detection means.

Figure 5:
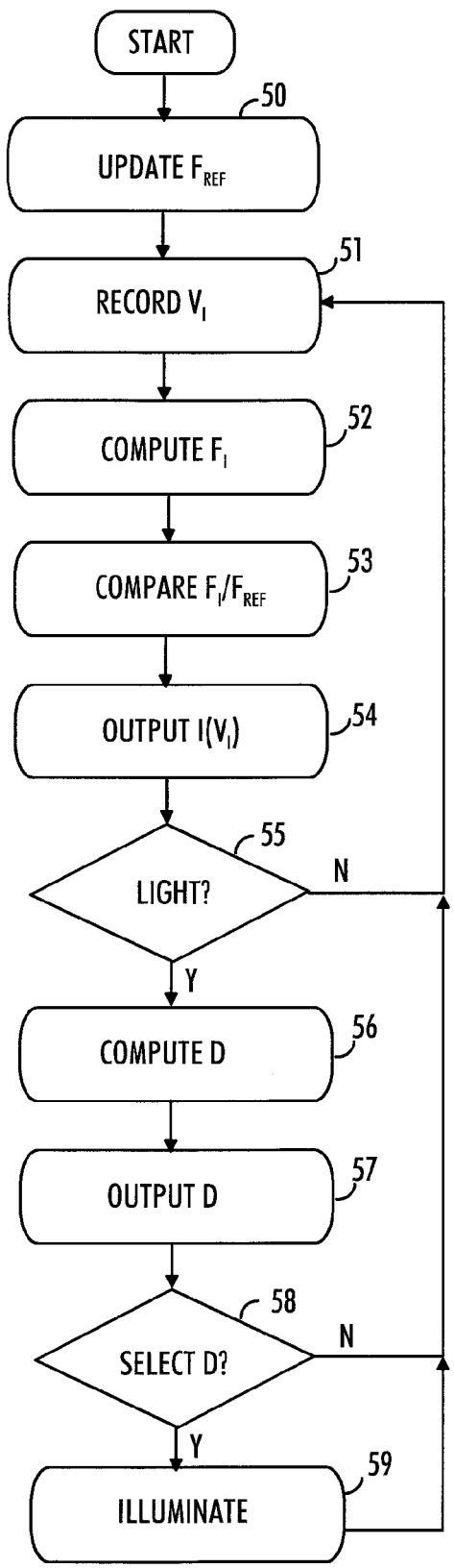
FIG. 5 illustrates a procedure implemented in an apparatus.

In an embodiment the interaction between the measuring and illumination means is interactive such that the light dose directed to the patient is adjustable according to temporal measurements results collected from the patient. Doses of light may vary in time, intensity, and spectrum. Accordingly, in the apparatus of FIG. 1, the processing means 110 may be configured to compute the dose to be emitted from the illumination means 120 in response the indication I(vi) generated by the measurement means 100 during the diagnostic session. The dose may be administered fully automatically, i.e. to take place without further authorization. On the other hand, the created adjustment may be output to the operator of the apparatus, but be released only after authorization and possible re-adjustment by the operator of the apparatus. FIG. 5 illustrates a procedure implemented in an apparatus of the latter option.

The apparatus performing the procedure of FIG. 5 comprises a user interface element for outputting information to the operator of the apparatus and for inputting instructions from the operator. The procedure incorporates the diagnostic session of FIG. 2 and an illumination session. Stages 50 to 54 correspond with stages 20 to 24 of FIG. 2. As discussed earlier, the indication $I(v_i)$ generated in stage 54 represents the level of medical disorder detected in the patient. The processing means comprise a threshold value $I_{th}$ against which the generated indication $I(v_i)$ is compared to decide (stage 55) whether light therapy is needed or not. If not, the procedure returns to stage 51 to be standby for a fresh set of voxel values. If yes, the indication $I(v_i)$ is used further to compute (stage 56) a dose D that corresponds with the level of medical disorder detected in the patient. The dose D is output (stage 57) to the operator of the apparatus. According to the choice of the operator (stage 58), the dose of light is then directed to the patient (stage 59) or the illumination is cancelled. After direction of the dose, or cancellation of the illumination, the procedure returns back to stage 51.

The data processing unit comprises a processor for performing systematic execution of operations upon data. The processor is an element that essentially comprises one or more arithmetic logic units, a number of special registers and control circuits. The processor typically comprises, or accesses a memory, data medium where computer-readable data or programs, or user data can be stored. The memory unit typically comprises volatile or non-volatile memory, for example EEPROM, ROM, PROM, RAM, DRAM, SRAM, firmware, programmable logic, etc. The processor performs systematic operations on data according to predefined, essentially programmed processes. The systematic operation of these units thus provides means for the procedures, or means for performing one or more stages of the procedures, which have been described in more detail with each respective embodiment in FIGS. 1 to 5.

In an embodiment, there is provided an apparatus comprising measuring means, such as the medical imaging unit, for generating a group of voxel values of a patient, a voxel value representing an electromagnetically detectable functional state in a brain voxel of the patient; detecting means, such as the data processing unit, for generating from the group of voxel values of the patient an indication that represents a level of a specific medical disorder of the patient; and illumination means, such as the illumination unit, for directing non-invasively a dose of light to the brain of the patient.

In general, various embodiments of the device may be implemented in hardware or special purpose circuits, software, logic or any combination thereof. Some aspects may be implemented in hardware, while some other aspects may be implemented in firmware or software, which may be executed by a controller, microprocessor or other computing device. Software routines, which are also called as program products, are articles of manufacture and can be stored in any device-readable data storage medium and they include program instructions to perform particular tasks. Thus the exemplary embodiments of this invention also include computer program products, readable by a computer and encoding instructions for executing a process in the light dispensing apparatus disclosed above.

It will be evident to a person skilled in the art that, as technology advances, the inventive concept can be implemented in various ways. The invention and its embodiments are not limited to the examples described above but may vary within the scope of the claims.

What is claimed is:

1. An integrated measurement and treatment apparatus, comprising:
    a medical imaging unit configured to generate a group of voxel values of a patient, a voxel value representing an electromagnetically detectable functional state in a brain voxel of the patient;
    a data processing unit configured to access a reference database storing reference data associated with a medical disorder related to functional states of internal structures in the brain related to seasonal affective disorder, the data processing unit further configured to generate an indication that indicates a level of similarity between the group of voxel values of the patient and the reference data, the level of similarity representing severity of the medical disorder; and
    an illumination unit configured to direct non-invasively a dose of light to the brain of the patient, wherein both the medical imaging unit and the illumination unit are applied on the patient during one treatment session, the treatment session comprising a sequence of operations performed with the same apparatus, the illumination unit being further configured to adjust parameters related to the dose of light according to the indication generated during the same treatment session, wherein the dose of light is adjusted in terms of at least one of intensity and spectrum.

2. An apparatus according to claim 1, wherein the reference data comprises a model representing functional connectivity of defined resting state networks considered relevant to the medical disorder.

3. An apparatus according to claim 2, wherein the reference data is based on measurements collected from a group of test subjects.

4. An apparatus according to claim 1, wherein the data processing unit is configured to:
    compare the voxel values of the patient with the reference data associated with the medical disorder; and
    generate, according to the level of similarity between the voxel values and the reference data, the indication.

5. An apparatus according to claim 4, wherein the comparison applies independent component analysis to estimate the level of similarity between the reference data and the voxel values of the patient.

6. An apparatus according to claim 1, wherein voxel values of the patient and the severity of the medical disorder of the patient are fed into the reference database.

7. An apparatus according to claim 1, wherein the medical imaging unit is configured to induce an electric or magnetic field into a measurement region, and the illumination unit is positioned to a protective distance from the measurement region, wherein the protective distance eliminates interference between the medical imaging unit and the illumination unit.

8. An apparatus according to claim 7, wherein the apparatus further comprises:
    a cradle for supporting the patient during the treatment session;
    a track for carrying the cradle between a measuring position and an illumination position;
    in the measuring position, the skull of the supported patient being within the measurement region; and
    in the illumination position the skull of the supported patient being outside the measurement region.

9. An apparatus according to claim 1, wherein the medical imaging unit is configured to induce an electric or magnetic field into a measurement region, and the illumination unit comprises a light transmission path that does not interact with the applied electrical or magnetic field in the measurement region.

10. An apparatus according to claim 9, wherein the light transmission path comprises a light source positioned outside the measurement region, and a light router providing non-interfering means for inputting a sequence of light from the light source and outputting the sequence of light inside the measurement region.

11. An apparatus according to claim 10, wherein the light router is a helmet configuration made of electromagnetically non-interfering materials and the light router comprises an optical collector, a first light router, an optical divider and a releasable headpiece.

12. An apparatus according to claim 11, wherein the optical collector is configured to absorb light from the light source and concentrate the absorbed light into a beam that progresses into a defined direction, the light router is configured to receive a light beam in one position and deliver the light beam along a defined route to another position, and the optical divider is configured to receive a light beam in one point and divide it into two or more beams that progress from the point of division along individual routes.

13. An apparatus according to claim 11, wherein the releasable headpiece comprises a rack of mechanically connected points of connection, and, during measurements, each point of connection is in a defined position.

14. A method comprising: generating a group of voxel values of a patient via medical imaging, a voxel value representing an electromagnetically detectable functional state in a brain voxel of the patient;
    accessing a reference database storing reference data associated with a medical disorder related to functional states of internal structures in the brain related to seasonal affective disorder;
    generating an indication that indicates a level of similarity between the group of voxel values of the patient and the reference data, the level of similarity representing severity of the medical disorder;
    directing non-invasively a dose of light to the brain of the patient, wherein both the medical imaging and the dose of light are applied on the patient during one treatment session, the treatment session comprising a sequence of operations performed with a same apparatus; and
    adjusting parameters related to the dose of light according to the indication generated during the same treatment session, wherein the dose of light is adjusted in terms of at least one of intensity and spectrum.

15. A method according to claim 14, the method further comprising:
    storing reference data associated with a medical disorder;

comparing the voxel values of the patient with the reference data associated to the medical disorder;

generating, according to the level of match between the voxel values and the reference data, the indication that represents a current level of that medical disorder of the patient.

16. A method according to claim 15, wherein the reference data comprises a model representing functional connectivity of defined resting state networks considered relevant in respect of the medical disorder.

17. A method according to claim 15, the method further comprising applying independent component analysis to estimate the level of match between the reference data and the voxel values of the patient.

18. A method according to claim 15, the method further comprising feeding voxel values of the patient and the detected level of a specific medical disorder of the patient into the reference database.

19. A non-transitory computer-readable medium comprising instructions that, when executed by a processing device, cause the processing device to perform operations comprising:

generating a group of voxel values of a patient via medical imaging, a voxel value representing an electromagnetically detectable functional state in a brain voxel of the patient;

accessing a reference database storing reference data associated with a medical disorder related to functional states of internal structures in the brain related to seasonal affective disorder;

generating an indication that indicates a level of similarity between the group of voxel values of the patient and the reference data, the level of similarity representing severity of the medical disorder;

directing non-invasively a dose of light to the brain of the patient, wherein both the medical imaging and the dose of light are applied on the patient during one treatment session, the treatment session comprising a sequence of operations performed with a same apparatus; and adjusting parameters related to the dose of light according to the indication generated during the same treatment session, wherein the dose of light is adjusted in terms of at least one of intensity and spectrum.

* * * * *